(12) United States Patent
Alexandersson

(10) Patent No.: US 11,318,256 B2
(45) Date of Patent: May 3, 2022

(54) INJECTION DEVICE

(71) Applicant: Carebay Europe Ltd., Sliema (MT)

(72) Inventor: Oscar Alexandersson, Haninge (SE)

(73) Assignee: SHL MEDICAL AG, Zug (CH)

( * ) Notice: Subject to any disclaimer, the term of this patent is extended or adjusted under 35 U.S.C. 154(b) by 72 days.

(21) Appl. No.: 16/093,431

(22) PCT Filed: Mar. 29, 2017

(86) PCT No.: PCT/EP2017/057439
§ 371 (c)(1),
(2) Date: Oct. 12, 2018

(87) PCT Pub. No.: WO2017/178237
PCT Pub. Date: Oct. 19, 2017

(65) Prior Publication Data
US 2021/0196896 A1    Jul. 1, 2021

(30) Foreign Application Priority Data
Apr. 16, 2016    (EP) .................................... 16169790

(51) Int. Cl.
*A61M 5/315*    (2006.01)
*A61M 5/32*    (2006.01)
*A61M 5/20*    (2006.01)

(52) U.S. Cl.
CPC .... *A61M 5/31513* (2013.01); *A61M 5/31501* (2013.01); *A61M 5/3202* (2013.01); *A61M 2005/206* (2013.01)

(58) Field of Classification Search
CPC .......... A61M 5/31513; A61M 5/31501; A61M 5/3202; A61M 5/2033; A61M 5/3204; A61M 2005/206; A61M 2005/202; A61M 2005/2086; A61M 2005/2477; A61M 2005/2481; A61M 5/20
See application file for complete search history.

(56) References Cited

U.S. PATENT DOCUMENTS

| 144,802 A | * | 11/1873 | Speak | ............... A61M 5/31513 604/222 |
| 2001/0002250 A1 | | 5/2001 | Burbank et al. | |
| 2014/0257193 A1 | * | 9/2014 | Bostrom | ............. A61M 5/3204 604/197 |

(Continued)

FOREIGN PATENT DOCUMENTS

| CN | 1636606 A | 7/2005 |
| CN | 101203255 A | 6/2008 |

(Continued)

*Primary Examiner* — Bhisma Mehta
*Assistant Examiner* — Neeraja Gollamudi
(74) *Attorney, Agent, or Firm* — McDonnell Boehnen Hulbert & Berghoff LLP

(57) ABSTRACT

Injection device comprising a housing having an insertion opening at its distal end, a syringe carrier arranged within said housing, an actuation sleeve that is slidably arranged in the housing, first and second energy accumulating members, a plunger holder that is operationally associated with the first energy accumulating member and the syringe carrier, and a plunger rod that is slidably arranged in relation to plunger holder and to the syringe carrier, the plunger rod being operationally associated with the second energy accumulating member.

18 Claims, 8 Drawing Sheets

(56) References Cited

U.S. PATENT DOCUMENTS

2014/0330216 A1* 11/2014 Weaver ............... A61M 5/3232
                                                      604/198
2017/0136189 A1*  5/2017 Tschirren .......... A61M 5/31553

FOREIGN PATENT DOCUMENTS

| CN | 103492000 A | | 1/2014 | |
|----|----|----|----|----|
| CN | 104582764 A | | 4/2015 | |
| WO | 2012045831 A1 | | 4/2012 | |
| WO | WO-2012045831 A | * | 4/2012 | .......... A61M 5/2033 |
| WO | 2012073035 A1 | | 6/2012 | |
| WO | 2012/117252 A1 | | 9/2012 | |
| WO | 2013032389 A1 | | 3/2013 | |

* cited by examiner

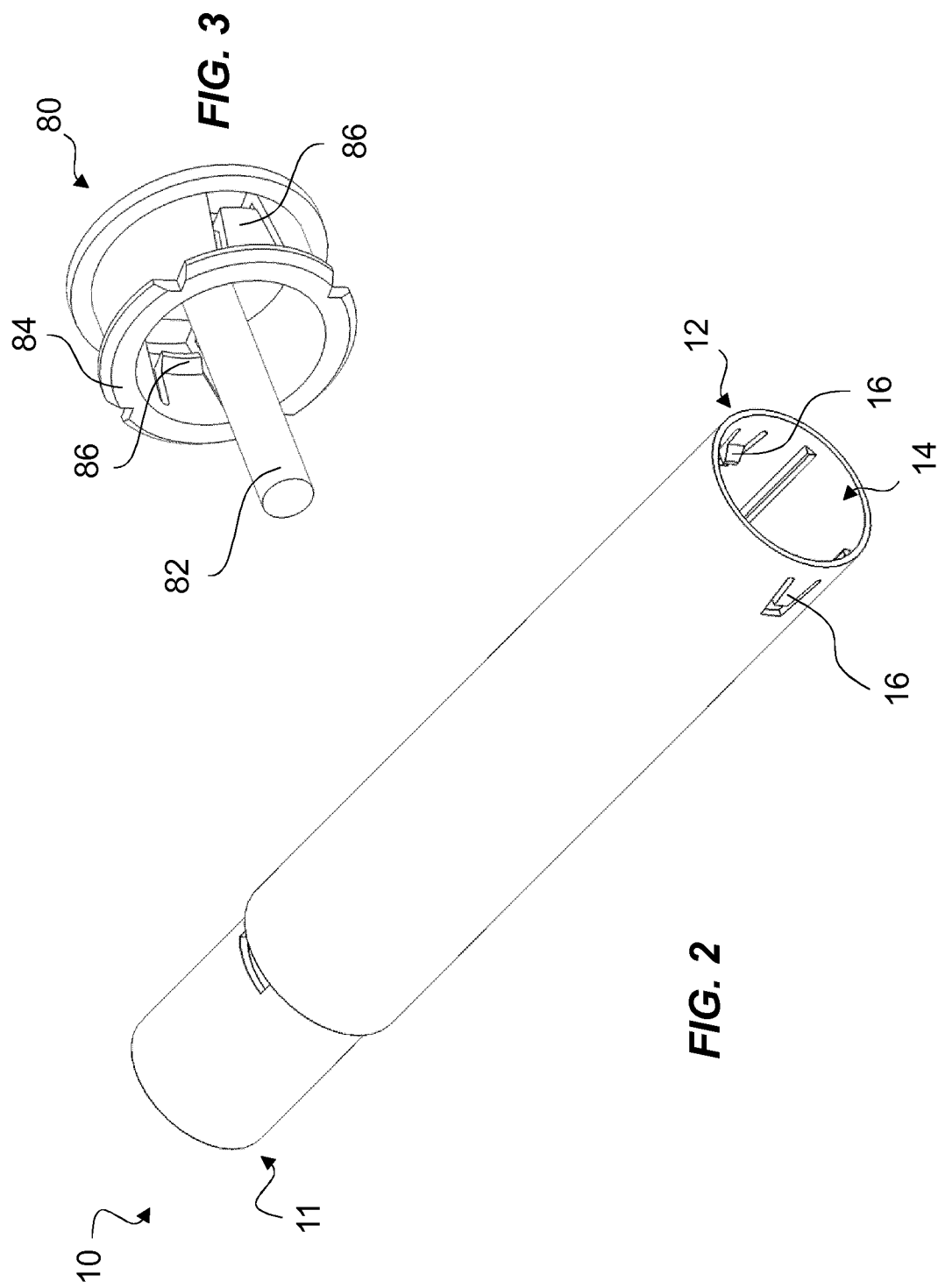

INJECTION DEVICE

CROSS REFERENCE TO RELATED APPLICATIONS

The present application is a U.S. National Phase Application pursuant to 35 U.S.C. § 371 of International Application No. PCT/EP2017/057439 filed Mar. 29, 2017, which claims priority to European Patent Application No. 16169790.9 filed May 16, 2016. The entire disclosure contents of these applications are hereby incorporated by reference into the present application.

TECHNICAL FIELD

The present invention relates to an injection device having several automatic functions such as automatic penetration, automatic injection and automatic safety means for preventing accidental needle sticks. More specifically, the present invention relates to a disposable, single use injection device having a mechanism that provides all these functions in a reliable and space-saving manner, but can be easily assembled.

RELATED ART

The present invention relates to injection devices for injecting a dose of medicaments or medicinal substances, such as insulin or hormones, in fluid form through a needle.

Auto-injectors, which are sometimes also referred to as pen-injectors, have been on the market for many years. One of the first auto-injectors was developed for war-times and was activated by pressing the injector against a body part. The main concern was to have the medicament injected as fast as possible without much concern for the patient or for handling safety aspects. During recent years some medicaments have been developed that have to be injected by the patients themselves. Therefore, depending on the intended use and type of medicament, injection devices having a varying degree of automatic functions have been developed to facilitate injection of medicaments in a reliable and safe manner for patients and even for trained personnel; e.g. physicians, nurses.

Auto-injector devices having a penetration function often comprise a housing, a container holder carrying a medicament container with a needle and a plunger rod as well as a spirally wound compression spring. When the devices are actuated, the container holder and the plunger rod, which are slidable in the housing, are jointly driven towards the patient's skin by the force of a compression spring. Thereby, penetration of the needle is effected. Known devices may be actuated by the user pressing a movable button. Actuation of the movable button may be inhibited until the device is positioned at a delivery site and a movable needle cover, which protrudes from the housing, is pushed against a patient's skin. However, many patients and practitioners prefer penetration to be automatic once the device is positioned at the delivery site.

Auto-injection devices having an automatic injection function often comprise an additional spirally wound compression spring acting on the plunger rod which in turn acts on a stopper inside a medicament container for expelling a medicament through the needle. The medicament is often injected following penetration once the container holder and the plunger rod are jointly moved to a predetermined position.

Some auto-injector devices may have an automatic safety function for preventing from accidental needle sticks by covering the needle with a needle cover when the device is withdrawn from the patient's skin.

Normally, auto-injection devices either do not provide all desired automatic functions and/or require several mechanisms with multiple individual movable parts, including small members and parts with complex shapes, in order to do so. However, this may lead to devices which do not provide all the functions desired by the patients and, moreover, devices which are larger than necessary and/or difficult to manufacture and assemble.

WO 2012/045831 A1 discloses an autoinjector comprising a first drive member configured to drive a first component in an axial direction, a second drive member configured to drive a second component in an axial direction, and a release mechanism configured to control a sequence of release of the first drive member and the second drive member, wherein the release mechanism is positioned at least partially within the first or second drive member.

WO 2012/073035 A1 discloses a delivery mechanism for an autoinjector comprising a first drive member configured to drive a first component in an axial direction, a second drive member configured to drive a second component in an axial direction, and a release mechanism configured to control a sequence of release of the first drive member and the second drive member, wherein the release mechanism is positioned at least partially within the first or second drive member.

The above-mentioned devices, however, rely on a comparably complex activation mechanism that includes multiple parts, that may be challenging to assemble and/or that may not provide all desirable safety features. There is thus an ongoing need in the art for injection devices that are easy to assemble during manufacture, simple to operate, reliable and safe.

In view of the above, it is an object of the present invention to provide a device that is easy to assemble during manufacture, simple to operate, reliable and safe.

SUMMARY OF THE INVENTION

In order to achieve one or several of the above-mentioned objects, an injection device according to independent claim 1 is provided. Further aspects, improvements and variations are disclosed in the dependent claims, the figures and the description.

According to a first aspect, the present invention relates to an injection device having a proximal end, a distal end, and a central longitudinal axis extending therebetween. In the present application, the term "distal" refers to the direction pointing away from a dose delivery site. When the term "distal part/end" is used, this refers to the part/end of the delivery device, or the parts/ends of the members thereof, which is/are located furthest away from the dose delivery site.

Correspondingly, the term "proximal" refers to the direction pointing to the dose delivery site. When the term "proximal part/end" is used, this refers to the part/end of the delivery device, or the parts/ends of the members thereof, which is/are located closest to the dose delivery site.

The injection device of the present invention comprises a housing (e.g. an outer housing) with a proximal end and a distal end, a carrier arranged within said housing, an actuation sleeve that is slidably arranged in the housing, a plunger holder, and a plunger rod. The carrier preferably is a syringe carrier configured for accommodating a syringe with a needle and a stopper that is sealingly and slidably arranged inside the syringe.

The plunger holder preferably is operationally associated with a first energy accumulating member and the carrier such that due to an output axial force from said first energy accumulating member, the plunger holder and the carrier are axially moveable in relation to the housing a predetermined distance towards the proximal end of the injection device from an initial position to a position in which the needle is protruded from the proximal end of the housing. In this latter position, the needle preferably is configured to be inserted into the user's skin when the injection device is held against a dose delivery site. A proximal end of the plunger holder and/or a distal end of the carrier may be ramped to facilitate assembly.

The first energy accumulating member preferably is arranged in the interior of the housing and adapted to accumulate and store energy. The first energy accumulating member preferably is supported against a surface that is fixed in relation to the housing. The first energy accumulating member may be at least partially arranged around the plunger holder. The first energy accumulating member may be, for example, a spirally wound compression spring, which may also be referred to as a penetration spring. The penetration spring preferably is biased in the initial position of the plunger holder. More specifically, the penetration spring preferably is at least partially compressed in this position.

The plunger rod preferably is slidably arranged in relation to plunger holder and to the carrier. Preferably, the plunger rod is operationally associated with the stopper of the carrier.

The plunger rod preferably is operationally associated with a second energy accumulating member such that due to an output axial force from said second energy accumulating member the plunger rod is axially moveable in relation to the plunger holder towards the proximal end of the injection device from a position preceding dose injection to a position following dose injection.

The second energy accumulating member preferably is arranged in the interior of the housing and adapted to accumulate and store energy. The plunger holder may be at least partially arranged around the second energy accumulating member. The second energy accumulating member may be arranged at least partially around the plunger rod. Also the second energy accumulating member may be, for example, a spirally wound compression spring. This spring may be referred to as a dose injection spring. The dose injection spring preferably is biased in the initial position of the plunger holder. More specifically, the dose injection spring preferably is at least partially compressed in this position.

The device according to the invention preferably comprises at least one first deflecting member. The at least one first deflecting member preferably is configured to substantially inhibit movement of the plunger holder towards the proximal end of the injection device when the plunger holder is in the initial position. The at least one first deflecting member may, for example, interact and/or mechanically engage with the plunger holder in order to substantially inhibit the plunger holder's movement. The at least one first deflecting member may be at least one deflecting lever, preferably at least one deflecting lever with a hook. The device may comprise at least two first deflecting members. The first deflecting member/s preferably is/are arranged in the distal half of the device when considering the device's total extension along its central longitudinal axis.

The first deflecting member/s may also be arranged in the distal half of the housing when considering the housing's total extension along its central longitudinal axis.

The first deflecting member preferably is configured to deflect when it is overlapped by an opening and/or recess of the actuation sleeve. The first deflecting member preferably is configured to deflect away from the central longitudinal axis.

The first deflecting member may elastically recoil and/or may be flexed aside by a ramped engagement with another element. In other words, the first deflecting member and/or the other element may be provided with a ramp such that the first deflecting member is flexed aside when the components are axially pushed against each other. The other component may be, in particular, the plunger holder, more specifically a collar of said plunger holder.

The first deflecting member preferably is configured to release the plunger holder when it deflects. Once the mechanical engagement between the first deflecting member and the plunger holder is released, the plunger holder preferably is free to be moved towards the proximal end of the injection device from the initial position to the position in which the needle is protruded from the proximal end of the housing by the output axial force of the first energy accumulating member.

The at least one first deflecting member may be formed integrally with a holding component. The holding component may be at least partially arranged around the plunger holder. The holding component may be arranged in the housing in a substantially fixed manner, in particular axially fixed. More specifically, the at least one first deflecting member may be formed integrally with a tubular portion of the holding component. This tubular holding component portion preferably is at least partially disposed between the actuation sleeve and the plunger holder. The actuation sleeve preferably is arranged at least partially around the holding component and axially movable in relation thereto. The holding component may be arranged in the rear/distal part of the device, for example, in the rear/distal half of the housing. In particular, the entire holding component may be arranged in the distal half of the device when considering the device's total extension along its central longitudinal axis. Alternatively or additionally, the holding component may be arranged in the assembled device such that it does not extend into a region corresponding to the most proximal third of the device or the proximal half of the device when considering the device's total extension along its central longitudinal axis. When the injection device comprises at least two first deflecting members, both first deflecting members may be formed integrally with the holding component.

The device according to the invention preferably comprises at least one second deflecting member. The at least one second deflecting member preferably is configured to substantially inhibit movement of the plunger rod towards the proximal end of the injection device when the plunger holder is in its initial position. More specifically, the at least one second deflecting member preferably is configured to substantially inhibit movement of the plunger rod relative to the plunger holder towards the proximal end of the injection device when the plunger holder is in the initial position. The at least one second deflecting member may, for example, interact and/or mechanically engage the plunger holder in order to substantially inhibit the plunger rod's movement. The at least one second deflecting member may be at least one deflecting lever, preferably at least one deflecting lever with a hook. The device may comprise at least two second deflecting members. The second deflecting member(s) may be integrally formed with the plunger rod.

The second deflecting member preferably is configured to deflect towards the central longitudinal axis such that the plunger rod is released from engagement with the plunger holder. Preferably, the second deflecting member is configured to deflect towards the central longitudinal axis when the plunger holder reaches the position following needle penetration.

The deflection of the second deflecting member towards the central longitudinal axis preferably is inhibited by a locking rod in the initial position of the plunger holder and/or until the plunger holder reaches the position following needle penetration. The locking rod preferably extends from the distal end of the device in a proximal direction. Preferably, the plunger rod is hollow and/or has an opening (e.g. a central opening) facing the distal end of the injection device. When the plunger holder is in the initial position, the locking rod preferably extends into the plunger rod. In other words, the plunger rod may at least partially surround the locking rod. The locking rod may also extend into the plunger holder. Therefore, also the plunger holder may at least partially surround the locking rod.

The second deflecting member may elastically recoil and/or may be flexed aside by a ramped engagement with another element. In other words, the second deflecting member and/or the other element may be provided with a ramp such that the second deflecting member is flexed aside when the components are axially pushed against each other. The other component may be, in particular, the plunger holder.

The housing preferably has an insertion opening at its distal end. In other words, the distal end of the housing preferably is open. The housing, in particular its insertion opening, preferably is configured to allow insertion of the assembled activation mechanism into the housing, preferably as a single sub-assembly. For example, at least one, several or all of the following elements may be configured to be inserted into the housing through the insertion opening: the carrier, the actuation sleeve, the holding component, the plunger holder, the first energy accumulating member, the plunger rod and/or the second energy accumulating member. In addition, also a needle cover, which will be described in more detail below, may be configured to be inserted into the housing through the insertion opening. Preferably, all these elements are configured to be inserted from the distal end of the injection device into the housing through the insertion opening as a single, pre-assembled sub-assembly, preferably in a single step.

The insertion opening preferably is closed by a distal end cap. The distal end cap preferably is inserted into the insertion opening from the distal end of the device, more preferably after all elements of the activation mechanism mentioned above have been inserted. The distal end cap may comprise a first lock feature (e.g., a lock protrusion or collar), that is engaged with a first locking feature (e.g., a hook) of the housing (or vice-versa). Alternatively or additionally, the distal end cap may comprise a second locking feature (e.g., lever with a hook) that is engaged with a second lock feature (e.g., an opening and/or recess) of the holding component (or vice-versa). The second locking feature and the second lock feature may lock the distal end cap and the holding component in an axially and/or rotationally fixed manner with respect to each other and may thereby lock the pre-assembled activation mechanism close. Preferably, the distal end cap may be coupled and/or fixed to the holding component before the pre-assembled activation mechanism is inserted into the housing.

The above-mentioned locking rod may be attached to and/or formed integrally with the distal end cap. The first energy accumulating member preferably bears and/or is supported against the distal end cap.

The injection device according to the invention preferably comprises a needle cover that is operationally associated and/or formed integrally with the actuation sleeve. Preferably, the needle cover is provided by a separate component that is coupled and/or operationally associated with said actuation sleeve, which may facilitate assembly of the injection device even further.

The needle cover may be arranged in the housing in an axially moveable manner. Preferably, the needle cover is axially movable in relation to the housing towards the distal end of the injection device from a starting position to a retracted position. The injection device may be configured such that moving the needle cover from the starting position to the retracted position activates the injection and/or dose delivery sequence. The device according to the invention may thus be configured to provide automatic penetration and/or dose delivery when pressed against the skin.

The needle cover may be operationally associated with the actuation sleeve such that the actuation sleeve is moved with the needle cover from a position in which the actuation sleeve substantially inhibits the deflection of the first deflecting member(s) to a position in which the opening and/or recess of the actuation sleeve overlaps the first deflection member(s), thus allowing the first deflection member(s) to deflect.

The needle cover may further be axially movable in relation to the housing towards the proximal end of the injection device from the retracted position to a position in which the needle is covered. In particular, the needle cover may be axially movable in relation to the housing from a retracted position to a position in which the needle is covered after use (i.e., after said needle has been protruded from the proximal end of the housing by moving the plunger holder and the carrier in the proximal direction during needle insertion). This position may thus also be referred to as a final position of the needle cover.

In the starting position of the needle cover, distal movement of the needle cover towards the proximal end of the injection device into the final position preferably is inhibited. Preferably, the needle cover and/or the actuation sleeve is/are mechanically engaged with the plunger holder. For example, the plunger holder may comprise a stop feature that is engaged with an opening and/or recess of the needle cover and/or with an opening and/or recess of the actuation sleeve. Movement of the needle cover towards the proximal end of the injection device from the starting position into the final position may thus be substantially inhibited by the plunger holder in the plunger holder's initial position. When the plunger holder reaches the position in which the needle is protruded from the proximal end of the housing, the needle cover preferably is allowed to move towards the proximal end of the injection device far enough to reach its final position.

The injection device may comprise a third energy accumulating member that is operationally associated with the actuation sleeve and/or the needle cover. Preferably, the actuation sleeve and/or the needle cover is axially moveable in relation to the housing towards the distal end of the injection device against an axial force from said third energy accumulating member. The actuation sleeve and/or the needle cover may also be axially moveable in relation to the housing towards the proximal end of the injection device by an output axial force from said third energy accumulating member. The needle cover may thus be moved from its starting position to its retracted position against the axial force of said third energy accumulating member while it may be moved from the retracted position to the final position by the axial force of said third energy accumulating member. The third energy accumulating member may be at least partially arranged around the plunger holder and/or around the plunger rod. The third energy accumulating member may be, for example, a spirally wound compression spring, which may also be referred to as a needle cover spring. A distal end portion of the third energy accumulating member may be supported against a surface that is fixed in relation to the housing, which preferably is a surface of the distal end cap.

The injection device may be configured to substantially inhibit axial movement of the needle cover in relation to the housing towards the distal end of the injection device when the needle cover reaches the final position. For example, the injection device may comprise at least one third deflecting member that substantially inhibits axial movement of the needle cover in relation to the housing towards the distal end of the injection device once the final position is reached.

The at least one third deflecting member may comprise at least one deflecting lever, preferably at least one deflecting lever with a hook. The deflecting lever could be formed integrally with the needle cover or with the housing and engage an opening and/or recess of the housing or an opening and/or recess of the needle cover, respectively.

According to a further aspect, the invention may relate to a method of assembling the injection device described above. This method may comprise inserting the needle cover, the carrier, the actuation sleeve, the holding component, the plunger holder, the first energy accumulating member, the plunger rod and/or the second energy accumulating member into the housing through the insertion opening at the distal end of the housing, wherein at least some or all of these elements preferably are pre-assembled as a sub-assembly during insertion.

BRIEF DESCRIPTION OF THE DRAWINGS

The invention will be described in more detail with reference to the figures below. These figures disclose an embodiment of the invention for illustrational purposes only. In particular, the disclosure provided by the figures is not meant to limit the scope of protection conferred by the invention.

FIG. 2 shows a perspective view of a housing of the injection device according to the preferred embodiment of FIG. 1;

FIG. 3 shows a perspective view of a distal end cap of the injection device according to the preferred embodiment of FIG. 1;

DETAILED DESCRIPTION OF THE DRAWINGS

Figure 1:
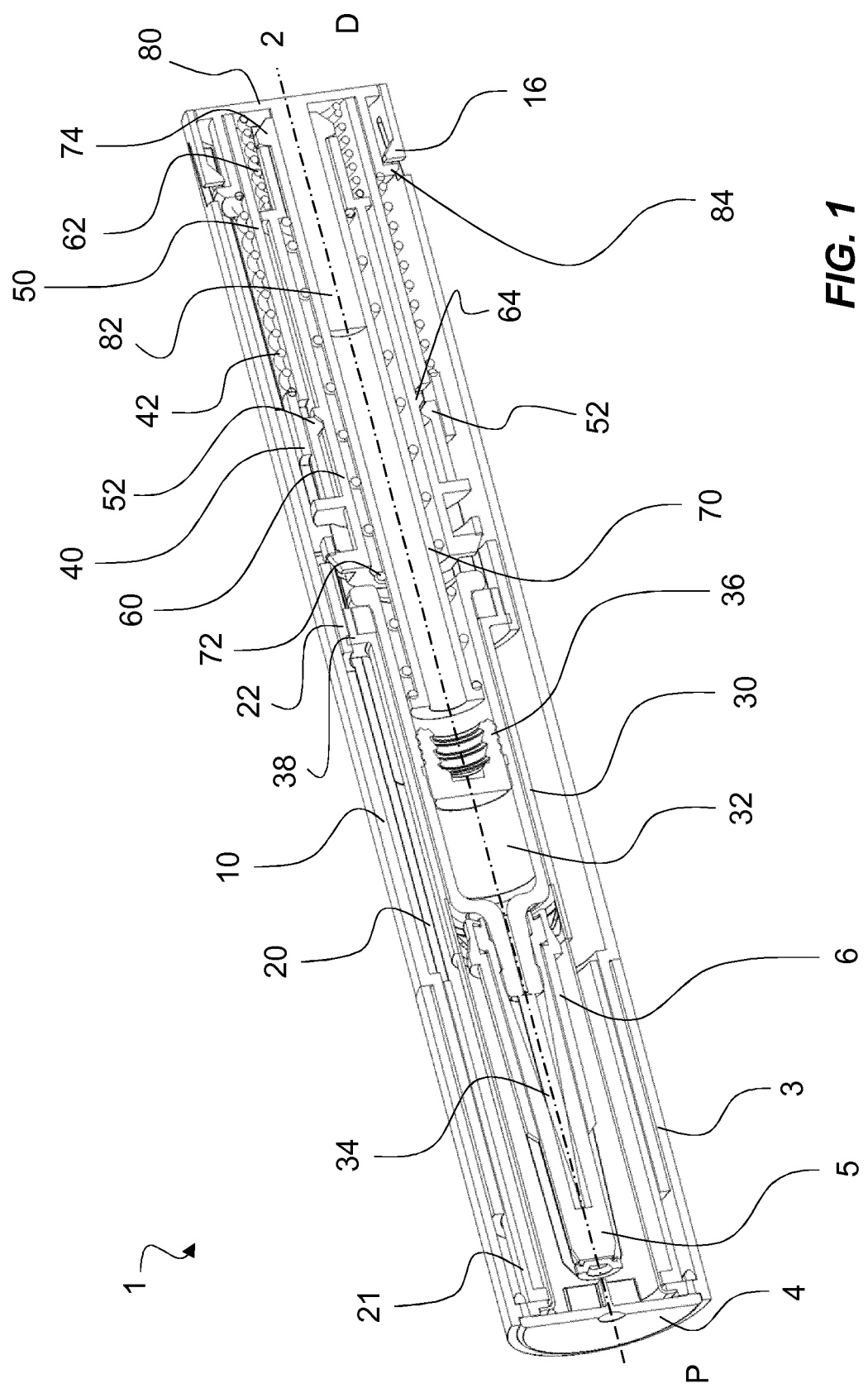
FIG. 1 shows a perspective cross-sectional view of an injection device according to a preferred embodiment of the invention, wherein a needle cover is in a starting position, wherein a plunger holder and a syringe carrier are in an initial position, and wherein a plunger rod is in a position preceding dose injection.

FIG. 1 shows an injection device 1 according to an exemplary embodiment of the invention before use. The device 1 has a proximal end P, a distal end D, and a central longitudinal axis 2 extending therebetween.

The device 1 comprises an outer housing 10. As shown in FIG. 2, the housing 10 has a proximal end 11 and an open distal end 12 that provides an insertion opening 14. With reference again to FIG. 1, the proximal end 11 of the housing 10 may be closed by a front cap 3 with a front closure 4. The distal end of the housing 10 may be closed with a distal end cap 80. As also shown in FIG. 3, the distal end cap 80 may be provided with a collar 84 as an exemplary first lock feature that engages with a first locking feature of the housing, which in the illustrative embodiment shown is a hooked lever 16. The distal end cap 80 may further be provided with a locking rod 82, which may be integrally formed with said distal end cap 80. The distal end cap 80 could also be referred to as a "distal cap".

As further shown in FIG. 1, a needle cover 20, a syringe carrier 30, an actuation sleeve 40, a holding component 50, a plunger holder 60, and a plunger rod 70 may be arranged within the housing 10. The syringe carrier 30 may accommodate a syringe 32 (which could also be referred to as a dose and/or a medicament container in the context of the present disclosure) that preferably is provided with a needle 34 at its proximal end. A stopper 36 may be sealingly and slidably arranged inside the syringe 32 to expel the medicament from the syringe 32 through the needle 34. The device 1 may be delivered with the needle 34 being covered by a needle shield 5. A needle shield remover 6 may be mounted in the front cap 3 and engage the needle shield 5 such that the needle shield 5 is retained in the front cap 3 when the device 1 is opened by removing the front cap 3.

The needle cover 20 may comprise a proximal section 21 and a distal section 22, the latter of which may be operationally associated with the actuation sleeve 40 such that needle cover 20 and the actuation sleeve 40 are axially slidable in the housing 10 towards the distal end D of the device 1.

The plunger holder 60 is operationally associated with the syringe carrier 30 and preferably mechanically engaged therewith. The plunger holder 60, furthermore, is operationally associated with a first energy accumulating member 62 (which in the illustrative example is a first compression spring) such that due to an output axial force from said first energy accumulating member 62 the plunger holder 60 and the syringe carrier 30 are axially moveable in relation to the housing 10 towards the proximal end P of the injection device 1. As shown in FIG. 1, the distal side of the first energy accumulating member 62 may bear against the distal end cap 80. The first energy accumulating member 62 may be at least partially compressed in the position illustrated in FIG. 1.

The plunger rod 70 is operationally associated with the stopper 36 and slidably arranged in relation to plunger holder 60 and to the syringe carrier 30. The plunger rod 70, furthermore, is operationally associated with a second energy accumulating member 72 (which in the illustrative example is a first compression spring) such that due to an output axial force from said second energy accumulating member 72 the plunger rod 70 is axially moveable in relation to the plunger holder 60 towards the proximal end P of the injection device 1. The second energy accumulating member 72 may bear against the plunger rod 70 on its proximal side and/or against the plunger holder 60 on its distal side. The second energy accumulating member 72 may be at least partially compressed in the position illustrated in FIG. 1.

FIG. 1 illustrates the device 1 before use with the needle cover 20 in a starting position and with the plunger holder 60 in an initial position. In the starting position of the needle cover, the actuation sleeve 40 at least partially surrounds the holding component 50, overlapping a portion of the holding component 50 that is provided with first deflecting members 52. These first deflecting members 52 may be provided by first deflecting levers with hooks that engage with a collar 64 of the plunger holder 60 and thereby inhibit movement of the plunger holder 60 towards the proximal end P of the injection device. A deflection of the first deflecting members 52 away from the central longitudinal axis 2 of the device 1 is prevented by the holding component 50.

Furthermore, as also shown in FIG. 1, movement of the plunger rod 70 relative to the plunger holder 60 towards the proximal end P of the injection device 1 is inhibited by second deflecting members 74. These second deflecting members 74 may be provided by second deflecting levers that are formed at the distal end of the plunger rod 70 and have a hook that engages the distal end of the plunger holder 60. In the initial position of the plunger holder illustrated in FIG. 1, a deflection of the second deflecting members 74 towards the central longitudinal axis 2 is prevented by the locking rod 82 extending into the distal end of the plunger rod 70.

After removing the front cap 3 and the needle shield 5, the needle cover 20 may be pressed against a dose delivery site (i.e., the skin of a user), whereby the needle cover 20 and the actuation sleeve 40 are moved towards the distal end D against an axial force of a third energy accumulating member 42 (which in the illustrative example is a third compression spring) from the starting position shown in FIG. 1 to a retracted position. The distal side of the third energy accumulating member 42 may bear against the distal end cap 80 while the proximal side may bear against the actuation sleeve 40.

Figure 12:
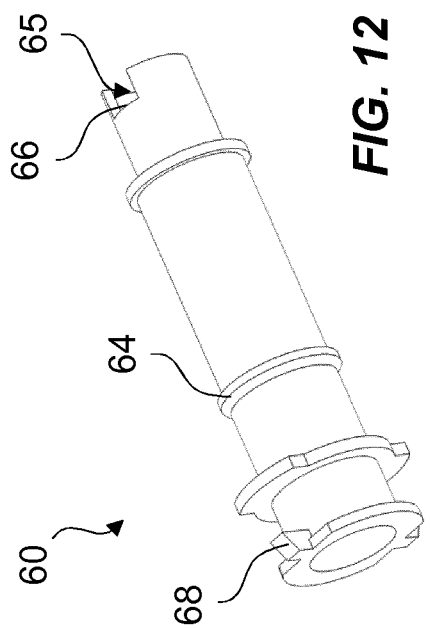
FIG. 12 shows a perspective view of a plunger holder according to the preferred embodiment of FIG. 1.

The third energy accumulating member 42 preferably is biased (i.e., at least partially compressed) in the starting position of the needle cover 20. The device 1, however, preferably is configured to substantially inhibit movement of the needle cover 20 towards the proximal end P of the device 1 when the plunger holder is in the initial position. This may be achieved, for example, by providing a mechanical engagement between the needle cover 20 and the syringe carrier 30 and/or the plunger holder 60. The mechanical engagement preferably is configured to allow a sliding movement of the needle cover 20 with respect to the syringe carrier 30 and/or the plunger holder 60, but limits proximal movement of the needle cover 20 beyond a certain point. In the illustrative example shown in the figures, the syringe carrier 30, which may be mechanically coupled to the plunger holder 60 by means of a protrusion 68 (see FIG. 12) extending into an opening of the syringe carrier 30, is provided with a stop 38 to limit proximal movement of the needle cover 20.

Figure 4:
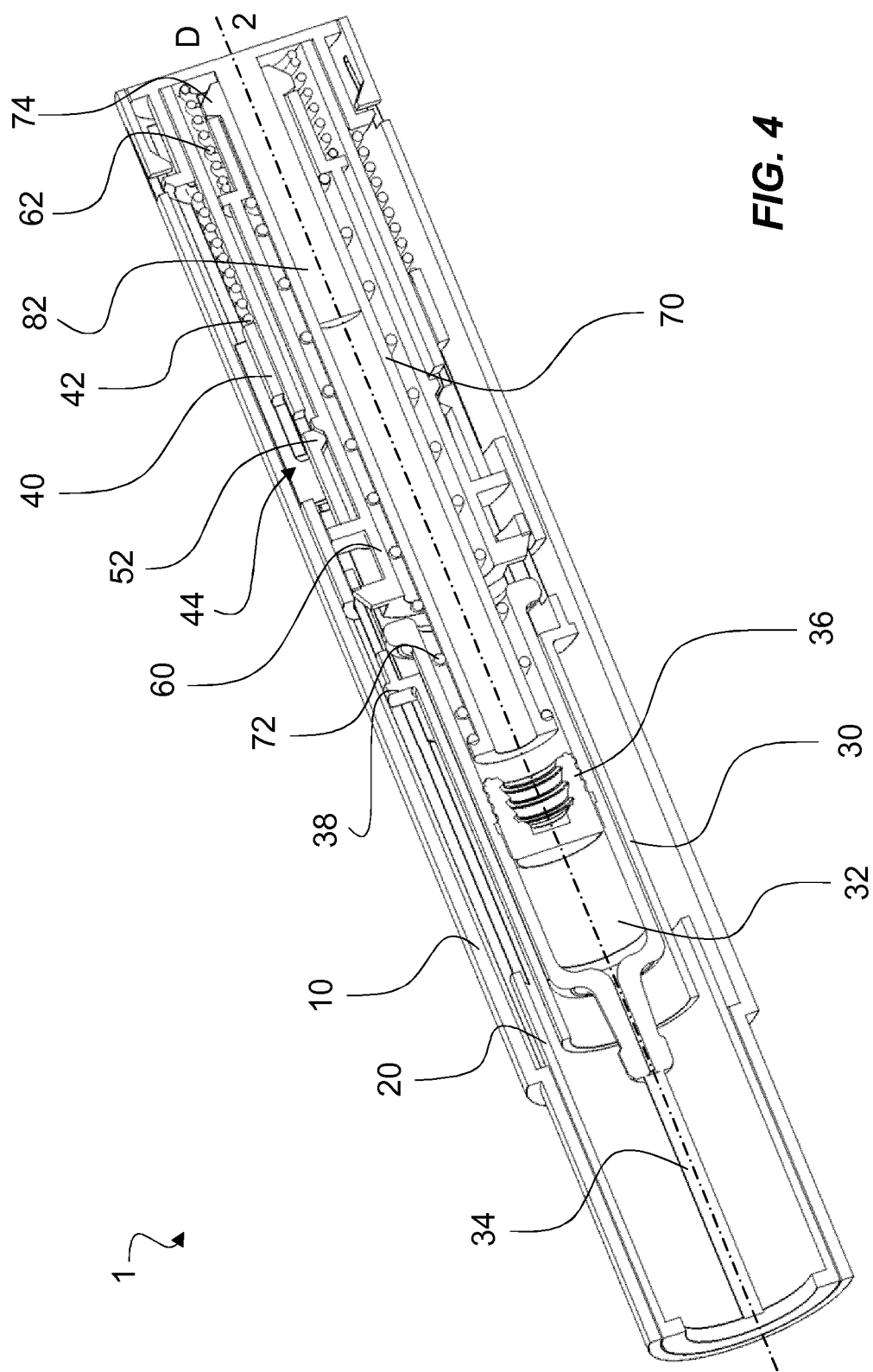
FIG. 4 shows a perspective cross-sectional view of the injection device according to the preferred embodiment of FIG. 1, wherein the needle cover has been moved from the starting position to a retracted position.

FIG. 4 illustrates the device 1 according to the preferred embodiment with the needle cover 20 and the actuation sleeve 40 in the retracted position. The front cap 3 and the needle shield 5 (not shown in FIG. 4) are removed.

As shown in FIG. 4, the actuation sleeve 40 is slit towards the distal end D of the device 1 such that the first deflecting members 52 are free to deflect outwardly. More specifically, the first deflecting members 52 are overlapped by openings 44 of the actuation sleeve 40. Preferably, the first deflecting members 52 and/or the collar 64 are ramped and the first deflecting members 52 are thus pressed outwardly by the output axial force of the first energy accumulating member 62, but the first deflecting members 52 may also be configured to recoil elastically. The actuation sleeve 40 and its openings 44 are illustrated in more detail in FIG. 11.

The syringe carrier 30 and the plunger holder 60 (with the plunger rod 70 retained therein) are thus free to be moved by the first energy accumulating member 62 in the proximal direction from their initial position shown in FIGS. 1 and 4 to a position in which the needle 34 is protruded from the proximal end of the housing 10, thereby performing needle penetration.

Figure 5:
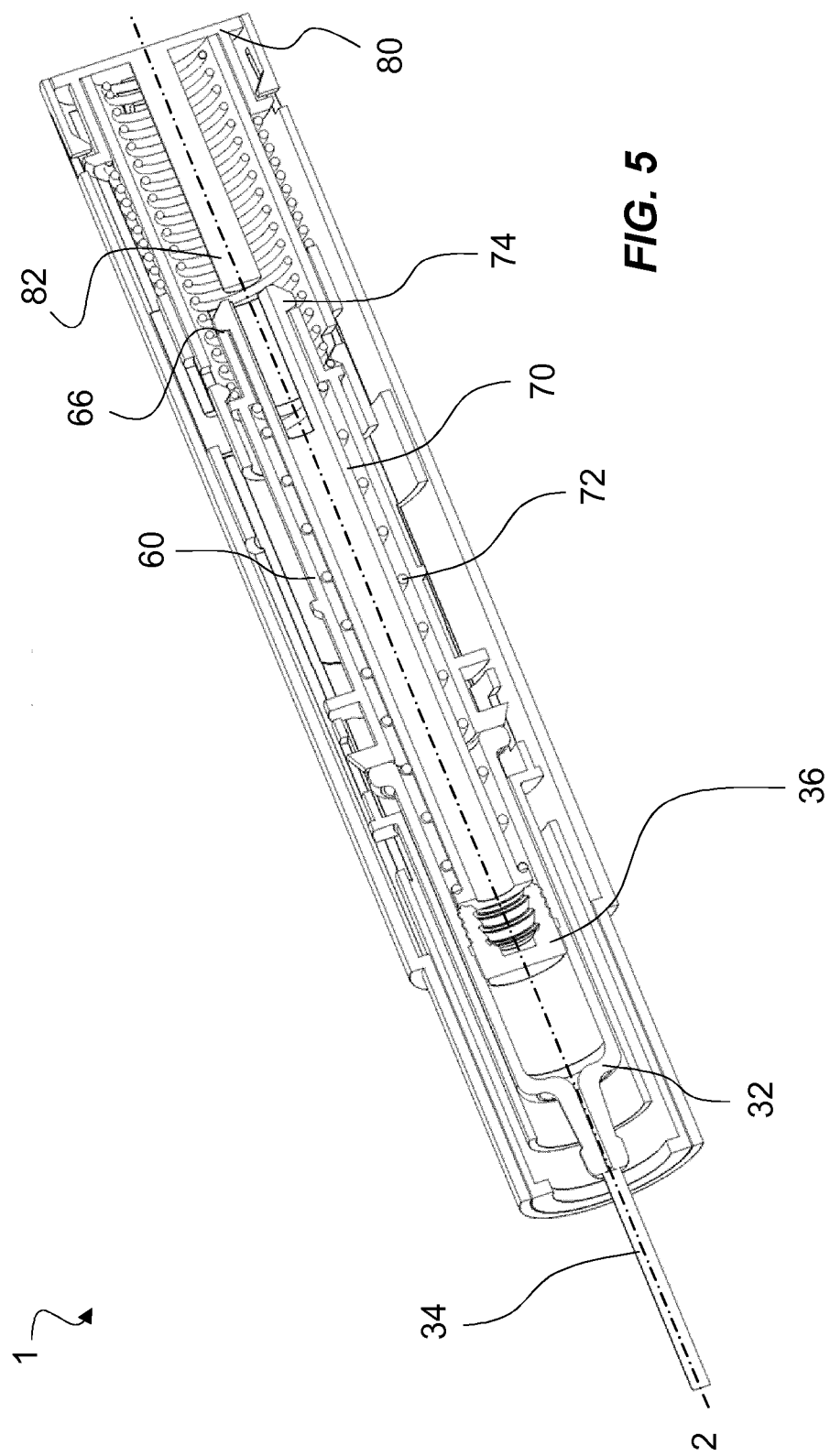
FIG. 5 shows a perspective cross-sectional view of the injection device according to the preferred embodiment of FIG. 1, wherein the plunger holder and the syringe carrier have been moved towards the proximal end of the injection device from the initial position to a position in which the needle is protruded from the proximal end of the housing.
Figure 13:
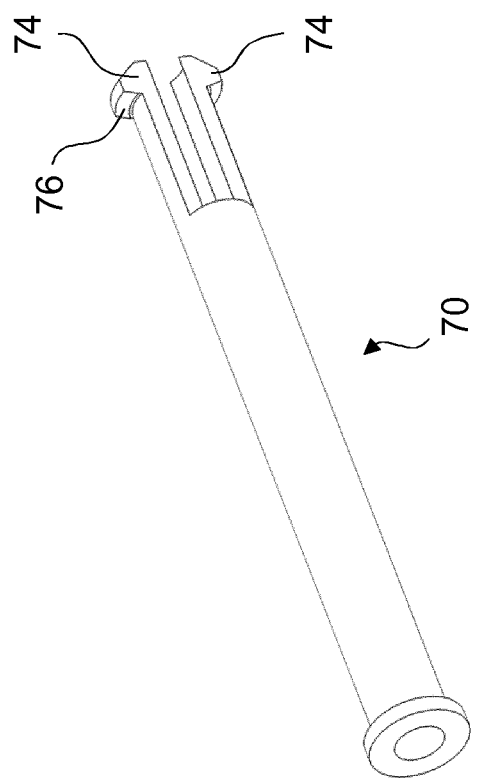
FIG. 13 shows a perspective view of a plunger rod according to the preferred embodiment of FIG. 1.

This position is shown in FIG. 5. As apparent therefrom, the second deflecting members 74 of the plunger rod 70 are moved past the proximal end of the locking rod 82. The second deflecting members 74 are thus free to deflect inwardly towards the central longitudinal axis 2. As shown, the second deflecting members 74 may be ramped and can thus be configured to be pressed inwardly towards the central longitudinal axis 2 by the output axial force of the second energy accumulating member 72. Alternatively or additionally, also a distal end portion of the plunger holder 60 may be ramped, for example the distal end wall 66 of a pocket 65 in which the second deflecting members 74 are retained. It is noted, however, that the second deflecting members 74 may also be configured to recoil elastically. The plunger holder 60 with its pockets 65 and the plunger rod 70 with a ramped surface 76 on each second deflecting member 74 are illustrated in more detail in FIGS. 12 and 13, respectively. The distal end portion of the plunger holder 60 may have a reduced inner diameter.

Figure 6:
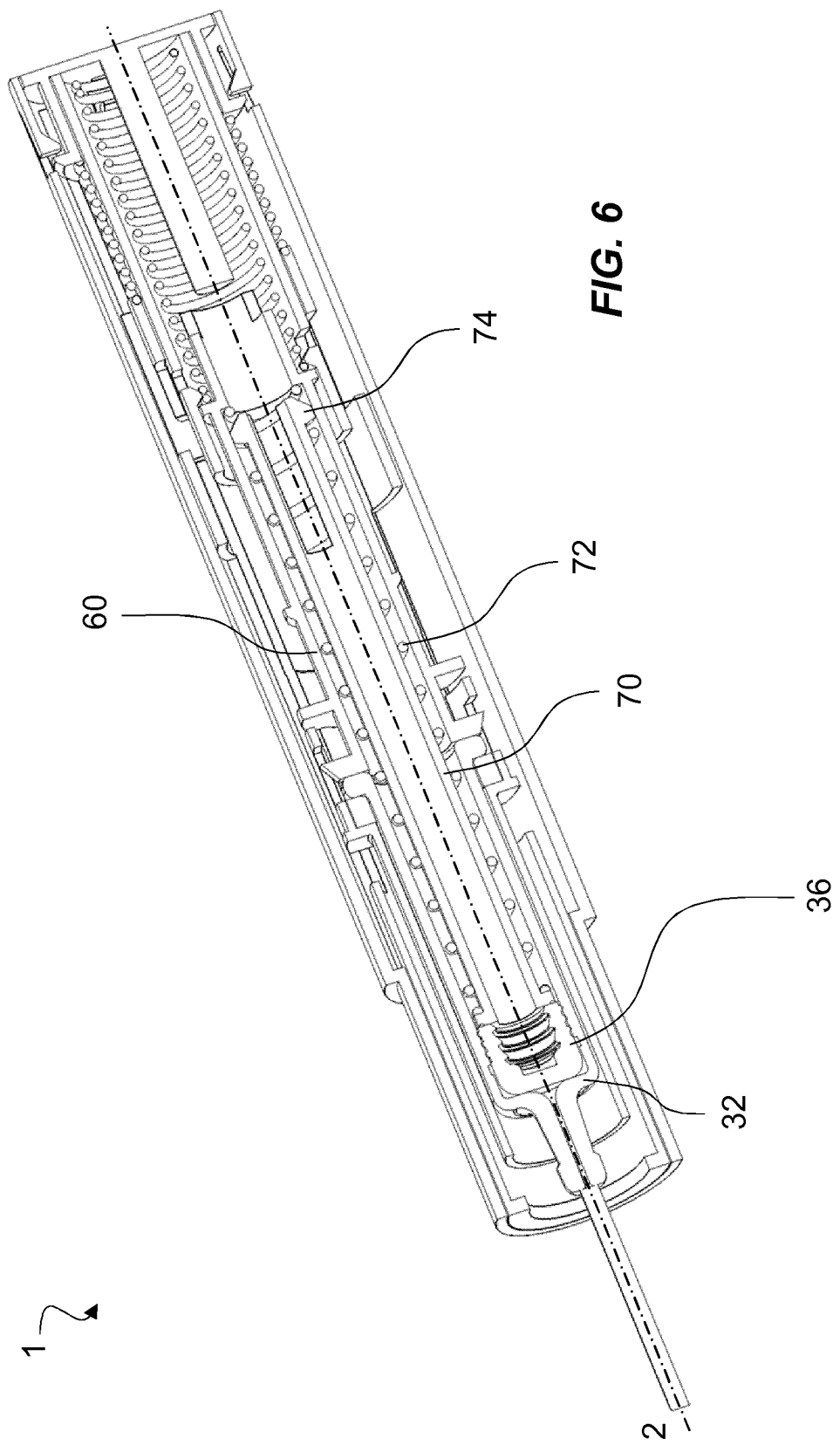
FIG. 6 shows a perspective cross-sectional view of the injection device according to the preferred embodiment of FIG. 1, wherein the plunger rod has been moved from the position preceding dose injection to a position following dose injection.

With the second deflecting members 74 being disengaged from the plunger holder 60, the plunger rod 70 is free to be moved in the proximal direction by the second energy accumulating member 72 from a position preceding dose injection shown in FIGS. 1, 4, and 5 to a position following dose injection, thereby moving the stopper 36 along the syringe 32 and ejecting the medicament or medicinal substance contained in the syringe 32 from the needle 34. FIG. 6 shows the device 1 in this position.

With the syringe carrier 30 being moved to the position in which the needle 34 is protruded from the proximal end of the housing 10, the needle cover 20 is free to be moved in the proximal direction by an output axial force of the third energy accumulating member 42 beyond its original starting position until it reaches a final position in which it fully covers the protruded needle 34. This position is shown in FIG. 7.

Figure 7:
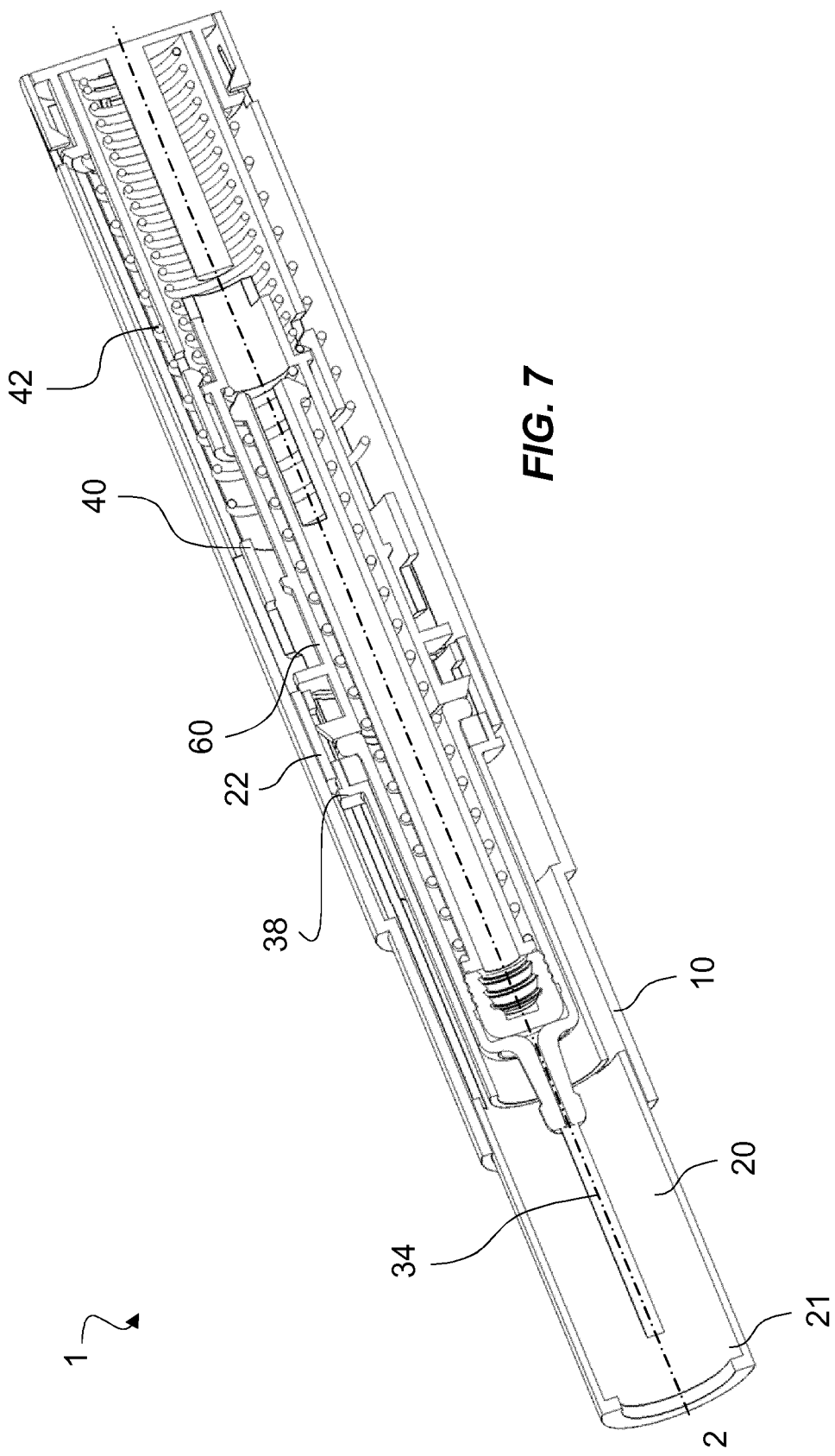
FIG. 7 shows a perspective cross-sectional view of the injection device according to the preferred embodiment of FIG. 1, wherein the needle cover has been moved from the retracted position to a final position.
Figure 8:
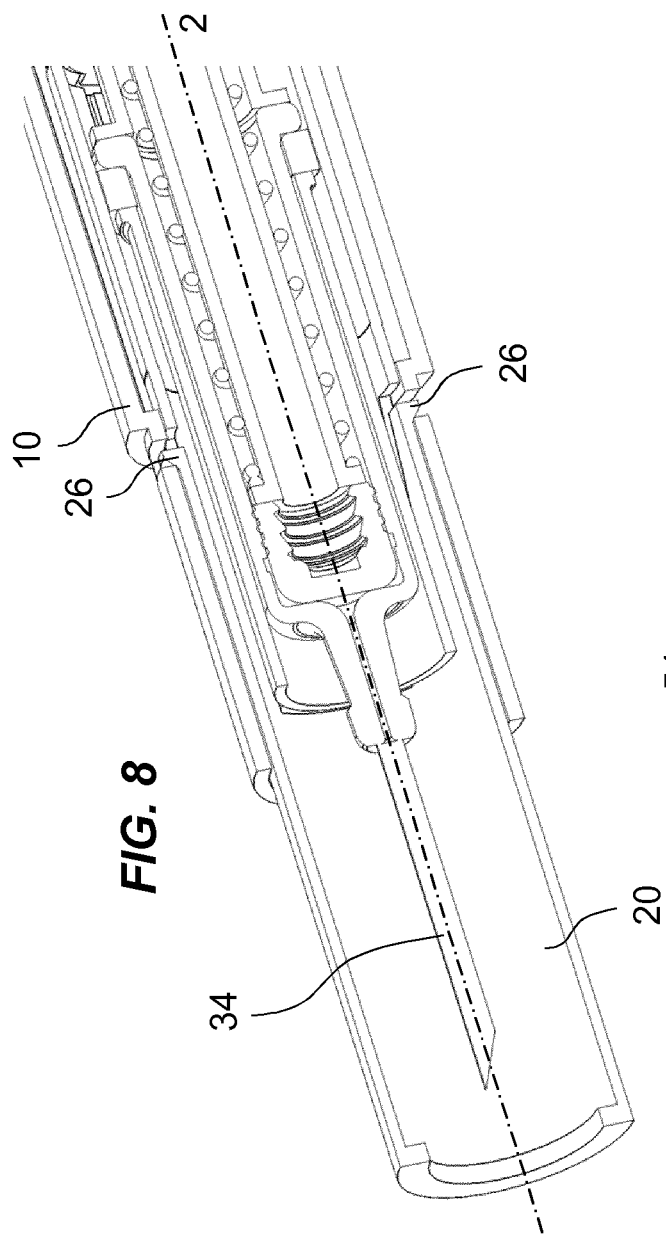
FIG. 8 shows a front portion of the injection device according to the preferred embodiment of FIG. 1 in the position of FIG. 7, with the cross-sectional plane of FIG. 7 being rotated by 90°.

FIG. 8 shows the device 1 in the same position as FIG. 7, but with the cross-sectional plane being rotated by 90°. As shown, the needle cover 20 may be provided with third deflecting members 26 that lock the axial position of the needle cover 20 with respect to the housing 10 once the needle cover 20 reaches the final position. In the illustrative example shown in figures, the third deflecting members 26 are provided by third deflecting levers that may have a hook, for example at their distal end.

Figure 9:
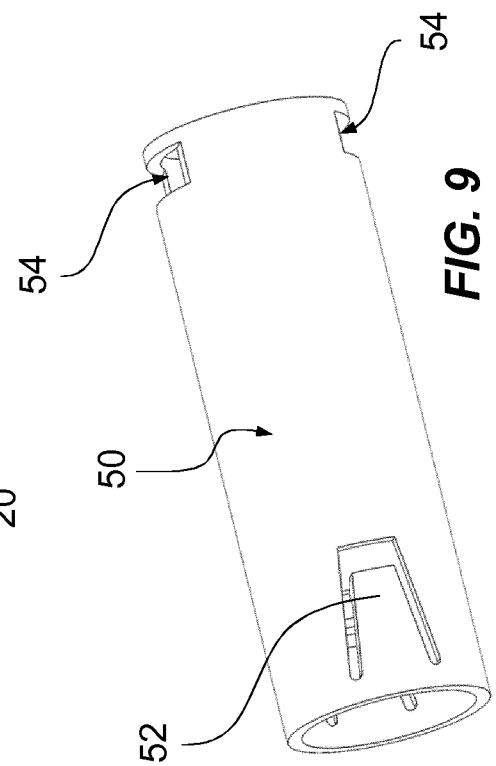
FIG. 9 shows a perspective view of a holding component according to the preferred embodiment of FIG. 1.

FIG. 9 shows the holding component 50. As apparent from this figure, the first deflecting members 52 may be integrally formed with a tubular portion of the holding component.

Figure 10:
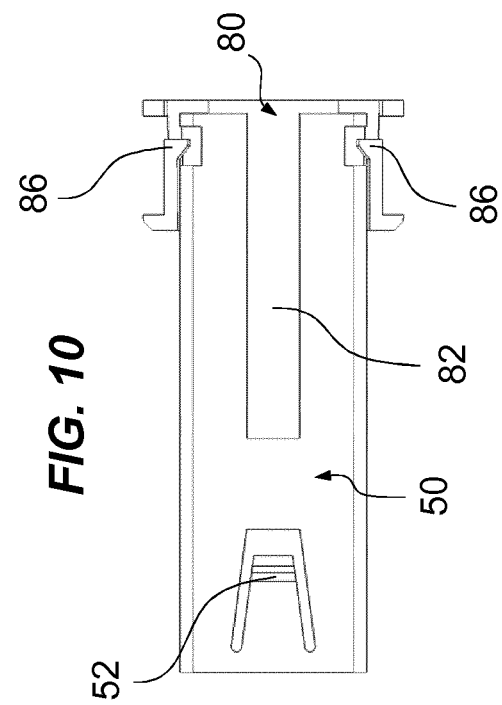
FIG. 10 shows a cross-sectional view of the holding component and the distal end cap of the injection device according to the preferred embodiment of FIG. 1 being engaged with each other in order to lock the assembled activation mechanism close.

As further shown in FIG. 9, the holding component 50 may further be provided with second lock features 54 that are provided as openings in the holding component 50 in the illustrative embodiment shown in the figures. The second lock features 54 may be engaged with second locking features 86 of the distal end cap, which in the illustrative embodiment of the figures are provided by levers with a hook (see FIG. 3). FIG. 10 illustrates the engagement of the second locking features 86 of the distal end cap 80 with the second lock features 54 of the holding component 50.

As will be apparent to the skilled person, the components of the activation mechanism (e.g., the needle cover 20, the syringe carrier 30, the actuation sleeve 40, the plunger holder 60, the plunger rod 70, the first energy accumulating member 62, the second energy accumulating member 72, and/or the third energy accumulating member 42) can be assembled together, inserted through the holding component 50, and then locked together with the distal end cap 80 before inserting the entire sub-assembly (i.e., the pre-assembled activation mechanism) into the housing 10.

Figure 11:
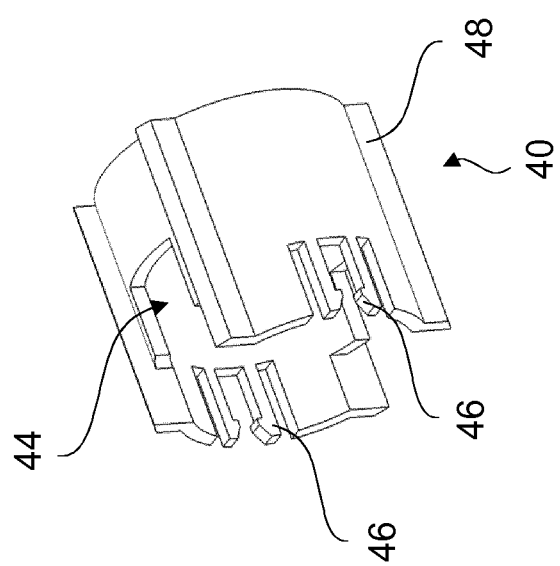
FIG. 11 shows a perspective view of an actuation sleeve according to the preferred embodiment of FIG. 1.

FIG. 11 shows the actuation sleeve 40 with the above-mentioned openings 44. As further illustrated in FIG. 11, the actuation sleeve 40 may also be provided with one or several engagement members 46 for coupling the actuation sleeve 40 to another element of the device, for example to the plunger holder 60 or the holding component 50. Thereby, premature activation of the device during transport and/or handling may be prevented. The one or several engagement members 46 could have one or several hooks configured to be released and/or opened by the needle cover 20 when the needle cover 20 moves towards the distal end D of the device. Furthermore the actuation sleeve 40 may be provided with guide members 48 that allow for movement of the actuation sleeve 40 in the housing 10 along the central longitudinal axis 2, but may inhibit rotation.

In view of the above, it will be apparent to the skilled person that the injection device 1 according to the present invention provides an activation mechanism that is reliable and safe and, in addition, easy to assemble during manufacture.

While aspects of the invention are illustrated and described in detail in the figures and in the foregoing description, such illustration and description is to be considered illustrative or exemplary and not restrictive. Also, reference signs in the claims should not be construed as limiting the scope.

It will also be understood that changes and modifications may be made by those of ordinary skill within the scope and spirit of the following claims. In particular, the present invention covers further embodiments with any combination of features from different embodiments described above. It is also to be noted in this context that the invention covers all further features shown in the figures individually, although they may not have been described in the previous or following description.

Whenever the word "comprising" is used in the claims, it should not be construed to exclude other elements or steps. Similarly, the indefinite article "a" or "an" does not exclude a plurality. A single unit may fulfill the functions of several features recited in the claims. It should also be understood that the terms "essentially", "substantially", "about", "approximately" and the like used in connection with an attribute or a value may define the attribute or the value in an exact manner in the context of the present disclosure. The terms "essentially", "substantially", "about", "approximately" and the like could thus also be omitted when referring to the respective attribute or value.

The invention claimed is:

1. An injection device, the injection device having a proximal end, a distal end, a central longitudinal axis, and comprising:

a housing with a proximal end and a distal end, the housing having an insertion opening at its distal end, a syringe carrier arranged within said housing, said syringe carrier being configured for accommodating a syringe with a needle and a stopper that is sealingly and slidably arranged inside said syringe;

an actuation sleeve that is slidably arranged in the housing;

a first energy accumulating member that is arranged in the interior of the housing and adapted to accumulate and store energy;

a second energy accumulating member that is arranged in an interior of the housing and adapted to accumulate and store energy;

a plunger holder that is operationally associated with said first energy accumulating member and the syringe carrier such that due to an output axial force from said first energy accumulating member, the plunger holder and the syringe carrier are axially moveable in relation to the housing a predetermined distance towards the proximal end of the injection device from an initial position to a position in which the needle is protruded from the proximal end of the housing;

a holding component comprising a tubular portion having at least one first deflecting member, where the holding component is partially disposed between the actuation sleeve and the plunger holder, and a plunger rod that is operationally associated with the stopper and slidably arranged in relation to the plunger holder and to the syringe carrier, wherein the plunger rod is operationally associated with the second energy accumulating member such that due to an output axial force from said second energy accumulating member the plunger rod is axially moveable in relation to the plunger holder towards the proximal end of the injection device from a position preceding dose injection to apposition following dose injection;

wherein, in the initial position of the plunger holder, movement of the plunger holder towards the proximal end of the injection device is substantially inhibited by the at least one first deflecting member interacting with the plunger holder, the at least one first deflecting member being configured to deflect when overlapped by an opening and/or recess of the actuation sleeve such that the plunger holder is released; and wherein, in the initial position of the plunger holder, movement of the plunger rod relative to the plunger holder towards the proximal end of the injection device is substantially inhibited by at least one second deflecting member, the at least one second deflecting member being configured to deflect towards the central longitudinal axis when the plunger holder reaches the position following needle penetration such that the plunger rod is released.

2. The injection device according to claim 1, wherein, in the initial position, the deflection of the at least one second deflecting member towards the central longitudinal axis is inhibited by a locking rod.

3. The injection device according to claim 1, wherein the insertion opening is closed by a distal end cap, wherein a locking rod is attached to and/or formed integrally with said distal end cap.

4. The injection device according to claim 1, wherein the injection device comprises a needle cover that is operationally associated and/or formed integrally with the actuation sleeve.

5. The injection device according to claim 4,
wherein the needle cover is axially moveable in relation to the housing;
wherein the needle cover is axially movable in relation to the housing towards the proximal end of the injection device from a retracted position to a final position in which the needle is covered; and
wherein, when the needle cover reaches the final position, axial movement of the needle cover in relation to the housing towards the distal end of the injection device is substantially inhibited.

6. The injection device according to claim 5, wherein, in the initial position of the plunger holder, movement of the needle cover towards the proximal end of the injection device from a starting position into the final position is substantially inhibited by the plunger holder and/or the syringe carrier interacting with the needle cover and/or the actuation sleeve.

7. The injection device according to claim 5, wherein, in the final position of the needle cover, axial movement of the needle cover in relation to the housing towards the distal end of the injection device is substantially inhibited by at least one third deflecting member.

8. The injection device according to claim 7, wherein the at least one third deflecting member comprises at least one deflecting lever, or at least one deflecting lever with a hook.

9. The injection device according to claim 1,
wherein the injection device further comprises a third energy accumulating member, the actuation sleeve being operationally associated with said third energy accumulating member;
wherein the actuation sleeve is axially moveable in relation to the housing towards the distal end of the injection device against an axial force from said third energy accumulating member and/or wherein the actuation sleeve is axially moveable in relation to the housing towards the proximal end of the injection device by an output axial force from said third energy accumulating member.

10. The injection device according to claim 1, wherein the holding component is at least partially arranged around the plunger holder and wherein the at least one first deflecting member is formed integrally with said holding component.

11. The injection device according to claim 1, wherein the at least one first deflecting member is formed integrally with the tubular portion of the holding component.

12. The injection device according to claim 1,
wherein the at least one first deflecting member comprises at least one deflecting lever, or at least one deflecting lever with a hook; and/or
wherein the at least one second deflecting member comprises at least one deflecting lever, or at least one deflecting lever with a hook.

13. The injection device according to claim 1, wherein a distal end portion of the first energy accumulating member is supported against a surface that is axially fixed in relation to the housing.

14. The injection device according to claim 1, wherein at least one, several or all of the following elements are configured to be inserted into the housing through the insertion opening: the needle cover, the syringe carrier, the actuation sleeve, the holding component, the plunger holder, the first energy accumulating member, the plunger rod and/or the second energy accumulating member.

15. The injection device according to claim 1,
wherein the first energy accumulating member is at least partially arranged around the plunger holder; and/or
wherein the plunger holder is at least partially arranged around the second energy accumulating member; and/or
wherein the plunger holder is arranged around the plunger rod.

16. A method of assembling an injection device comprises the steps of:
providing a housing with a proximal end and a distal end of the housing having an insertion opening at its distal end,
inserting an actuation sleeve, a holding component, a plunger holder and a plunger rod through the insertion opening into the housing,
wherein the holding component comprises a tubular portion having at least one first deflecting member and is partially disposed between the actuation sleeve and the plunger holder,
wherein the plunger rod comprises a second deflecting member that prevents movement of the plunger rod relative to the plunger holder and where the plunger rod is positioned within and axially movable relative to the plunger holder such that the plunger holder is initially prevented from proximal axial movement towards the proximal end of the housing by the at least one first deflecting member interacting with the plunger holder, and
wherein the second deflecting member deflects towards the central longitudinal axis when the plunger holder reaches a position following needle penetration such that the plunger rod is released.

17. The method of assembling the injection device according to claim 16, wherein
assembling the actuation sleeve, the plunger holder, and the plunger rod, together thus forming a pre-assembled activation mechanism.

18. The method of assembling the injection device according to claim 16, wherein
- inserting the actuation sleeve, the plunger holder, the plunger rod, through the holding component,
- locking a distal end cap to the actuation sleeve, the plunger holder, or the plunger rod, to form a sub-assembly, and
- inserting the sub-assembly into the housing.

* * * * *